United States Patent [19]

Blissard et al.

[11] Patent Number: 5,750,383
[45] Date of Patent: May 12, 1998

[54] BACULOVIRUS CLONING SYSTEM

[75] Inventors: Gary W. Blissard; Scott C. Monsma, both of Ithaca, N.Y.

[73] Assignee: Boyce Thompson Institute for Plant Research, Inc., Ithaca, N.Y.

[21] Appl. No.: 645,863

[22] Filed: May 14, 1996

[51] Int. Cl.$^6$ .......................... C12N 15/10; C12N 15/86; C12N 5/10
[52] U.S. Cl. ...................... 435/172.3; 435/235.1; 435/320.1; 435/348
[58] Field of Search ................ 435/172.3, 172.1, 435/325, 348, 320.1, 69.1, 235.1

[56] References Cited

U.S. PATENT DOCUMENTS

| | | | |
|---|---|---|---|
| 4,879,236 | 11/1989 | Smith | 435/320.1 |
| 5,143,905 | 9/1992 | Sivasubramanian et al. | 514/21 |
| 5,155,037 | 10/1992 | Summers | 435/348 |
| 5,162,222 | 11/1992 | Guarino | 435/348 |
| 5,169,784 | 12/1992 | Summers et al. | 435/320.1 |
| 5,244,805 | 9/1993 | Miller | 435/320.1 |
| 5,278,050 | 1/1994 | Summers | 435/69.1 |
| 5,306,628 | 4/1994 | Sivasubramanian et al. | 435/69.7 |

OTHER PUBLICATIONS

Hashimoto et al., J. gen. Virol., vol. 77, pp. 555–563, 1996.
Tanada et al., "Baculoviridae, Granulosis Viruses", in Atlas of Invertebrate Viruses, J.R. Adams and J.R. Bonami, Eds., CRC Press, 1991, pp. 250–257.
Huger et al., "Baculoviridae. Nonoccluded Baculoviruses", in Atlas of Invertebrate Viruses, J.R. Adams and J.R. Bonami, Eds., CRC Press, 1991, Chapter 9, pp. 287–319.
Boublik, Y, et al, 199. "Eukaryotic Virus Display: Engineering the Major Surface Glycoprotein of the *Autographa californica* Nuclear Polyhedrosis Virus (NcNPV) for the Presentation of Foreign Proteins on the Virus Surface" Bio/Tech., vol. 13, pp. 1079–1084.
Goswami, B et al, 1991, "A Simplified Method for the Production of Recombinant Baculovirus", BioTechniques, vol. 10, pp. 626–629.
Cartier, J et al, 1994, "Suppression of Apoptosis in Insect Cells Stably Transfected with Baculovirus p3: Dominant Interference by N–Terminal Sequences pp. 351–376", Jnl. Of Virology, pp. 7728–2237.
Jarvis, D et al, 1990, "Use of Early Baculovirus Promoters for Continuous Expression and Efficient Processing of Foreign Gene Products in Stably Transformed Lepidopteran Cells", Bio/Technology, vol. 8, pp. 950–955.
Davies, A. H., 1995, "Baculophage A New Tool For Protein Display", Bio/Technology, vol. 13, p. 1046.
Jarvis, D.L., 1993, "Effects of Baculovirus Infection on 1E1–Mediated Foreign Gene Expression in Stably Transformed Insect Cells", Jnl. Of Virology, pp. 2583–2591.
Hill, J et al, 1994, "Identification of the gp67 gene of a baculovirus pathogenic to the spruce budworm, *Choristoneura fumiferana* multinucleocapsid nuclear polyhedrosis virus", Jnl of General Virology, pp. 1881–1813.

Whitford, M et al, 1989, "Identification and Sequence Analysis of a Gene Encoding gp67, an Abundant Envelope Glycoprotein of the Baculovirus *Autographa californica* Nuclear Polyhedrosis Virus", Jnl of Virol, pp. 1393–1399.
Hohmann, A et al, 1983, "Monoclonal Antibodies to Baculovirus Structural Proteins: Determination of Specificities by Western Blot Analysis", Virology 125, pp. 432–444.
Volkman, L.E., 1986, "The 64K Envelope Protein of Budded *Autographa californica* Nuclear Polyhedrosis Virus" Microbiology and Immunology, vol. 131, pp. 103–118.
Bissard, G et al, 1990, "Baculovirus Diversity and Molecular Biology" Annu. Rev. Entomol., 35: 127–155.
Blissard, G et al, 1989, "Location, Sequence, Transcriptional Mapping, and Temporal Expression of the gp64 Envelope Glycoprotein Gene of the *Orgyis pseudotsugata* Milticapsid Nuclear Polyhedrosis, Virus", Virology 170 pp. 537–555.
Bishop, D et al, 1995, "The BacVector System: Simplified Cloning and Protein Expression Using Novel Baculovirus Vectors", No. 4, Dec. issue, pp. 1–6.
Noguchi, Y., 1995, "Isolateion and characterizaton of Temperature Sensitive Mutants of Bombyx Mori Nuclear Polyhedrosis Virus and Their Multiplication In a Cell Line and larvae of Bombyx Mori.", Inl of Sencultureal Scient of Japan, 64(3), pp. 230–236.
McLachlin J. Et al, "Identification and Characterization of vlf–1, a Baculovirus Gene Involved in Very Late Gene Expression", Jnl of Virology, 68(12) pp. 7746–7756.

(List continued on next page.)

*Primary Examiner*—David Guzo
*Attorney, Agent, or Firm*—Brown, Pinnisi & Michaels P.C.

[57] ABSTRACT

Disclosed herein is a novel baculovirus cloning system. The new cloning system is a marker-rescue system, using an essential gene, e.g. gp64. In this system, a gene essential for viral replication, growth, or propagation in cell culture is removed from or inactivated in the viral genome. Once a null baculovirus is created, it is propagated in a host cell that expresses the essential protein or a functional homolog. For cloning into the baculovirus containing the null-mutation, the virus is used to infect wild type host cells and the same cells are transfected with a plasmid that contains the essential gene, or a functional homolog, linked to a foreign gene under the control of a selected promoter. The baculovirus is "rescued" by the rescue gene linked to the foreign gene and is able to propagate normally and express the foreign gene. The recombinant "rescued" baculovirus can be used for gene expression, biological control or presentation of a foreign protein on the surface of the virus for vaccines and antibody production. As an example of this new cloning system, disclosed herein are recombinant baculoviruses that contain an insertionally inactivated or deleted gp64 efp gene, a gene that encodes a protein essential for viral infectivity and propagation in cell culture and in animals. To generate the virus the GP64 EFP protein was supplied in trans, from a stably transfected cell line. Homologous recombination was the used to generate inactivated gp64 efp genes in the context of otherwise wild type AcMNPV baculoviruses.

13 Claims, 4 Drawing Sheets

OTHER PUBLICATIONS

Birnbaum, M. Et al, 1994, "An Apopttosis–inhibiting Gene From A Nuclear Polyhedrosis Virus Encoding A Polypeptide With Cys–His sequence motifs", Jnl of Virology, 68(4), pp. 2521–2528.

Zaho, Y et al, 1994, "Complementation of human Immunodeficiency Virus (HIV–1) Gag Particle Formation", Virology 199 (2), pp. 403–408.

Hershberger, P et al, Site–Specific Mutagenesis of athe 35–Kilodalton Protein Gene Encoded by *Autographa californica* Nuclear Polyhedrosis Virus Cell Line—Specific Effects On Virus Replication, Jnl of Virol, 66 (9), pp. 5525–5533, 1992.

Figure 4 vAc-64Z (*gp64*-null AcMNPV)

*gp64*   Foreign Gene

GP64 Rescue Is Linked to Insertion
of a Foreign Gene

Host cells infected with the gp64-null virus are
transfected with a plasmid that contains:
a. the native gp64 gene and promoter linked to
b. a foreign gene under the control of a selected
   promoter (early, late, very late, or a
   combination).

Virion production rescued by
gp64 gene linked to a foreign gene

Utilization of Recombinant Baculovirus
for Gene Expression or Biological Control

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "PCR primer"

( x i ) SEQUENCE DESCRIPTION: SEQ ID NO:1:

GAGCTGATCG ACCGTTGGGG    20

( 2 ) INFORMATION FOR SEQ ID NO:2:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "PCR primer"

( x i ) SEQUENCE DESCRIPTION: SEQ ID NO:2:

CGGTTTCTGA TCATACAGTA CA    22

( 2 ) INFORMATION FOR SEQ ID NO:3:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "PCR primer"

( x i ) SEQUENCE DESCRIPTION: SEQ ID NO:3:

CCAGCGGCTG GTCGTTTATC GCCC    24

BACULOVIRUS CLONING SYSTEM

ACKNOWLEDGMENT OF GOVERNMENT SUPPORT

This invention was made with government support under Grant No. AI 33657, awarded by the National Institutes of Health. The government has certain rights in the invention.

FIELD OF THE INVENTION

The invention pertains to the field of baculovirus cloning systems. More particularly, the invention pertains to a cloning system that uses a baculovirus containing a deletion in an essential gene and the use of a stably transformed cell line to produce (and complement) production of virions that are used for marker-rescue cloning.

BACKGROUND OF THE INVENTION

Baculoviruses are large double stranded DNA viruses that are pathogens of insects. Infection of the host begins when insect larvae acquire the virus orally. Infection is first observed in the epithelial cells of the midgut and is followed in most cases by systemic infection. One hallmark of the baculovirus infection cycle is the production of two structurally and functionally distinct virion phenotypes. One virion phenotype, the occlusion derived virus (ODV), is found within the protective occlusion bodies. Once released from the occlusion body by the alkaline pH of the gut, the ODV initiates infection of the animal by infecting epithelial cells of the midgut. A second virion phenotype, the budded virus (BV), is produced by budding from the surface of infected cells. The BV is initially produced from infected midgut epithelial cells and is essential for systemic infection, mediating movement of the virus from midgut to other tissues and propagating the infection from cell to cell within the infected animal. BV are highly infectious to tissues of the hemocoel and to cultured cells, whereas ODV appear to be less infectious in cell culture or when injected into the hemocoel. The two virion phenotypes also differ in entry mechanisms, as the BV enter cells via endocytosis, while the ODV appear to fuse directly with the plasma membrane at the cell surface.

The major envelope protein of the BV is the GP64 Envelope Fusion Protein (GP64 EFP, also known as GP64 or GP67), which is an extensively processed type I integral membrane glycoprotein that has been studied in some detail. Densely packed peplomers found on the surface of BV are believed to be composed of the GP64 EFP protein and these peplomers are acquired by the virion during budding. Recent studies of a soluble form of GP64 EFP indicate that the native form of GP64 EFP is trimeric and thus, each peplomer is likely comprised of a single trimer of GP64 EFP. The important role of GP64 EFP in BV infectivity is demonstrated by the neutralization of BV infectivity with antibodies specific to GP64 EFP. Using syncytium formation assays and cells expressing gp64 EFP, it was shown that the GP64 EFP protein is both necessary and sufficient for low pH activated membrane fusion activity. In addition, two functional domains have been identified in GP64 EFP: an oligomerization domain necessary for trimerization and transport, and a small internal hydrophobic membrane fusion domain. Thus, functional studies of GP64 EFP show that GP64 EFP mediates membrane fusion in a pH dependent manner, consistent with an essential role for GP64 EFP during viral entry by endocytosis.

While indirect data on the role of GP64 EFP in the infection cycle strongly suggest that GP64 EFP is essential for infectivity of the BV, conclusive data have been lacking. No temperature sensitive mutants in the gp64 EFP gene are known, and previous attempts to generate a helper-independent virus containing a gp64 EFP deletion were unsuccessful. To demonstrate the essential nature of gp64 EFP and to further characterize the role of GP64 EFP in infection, we generated a stably-transfected cell line that constitutively expresses the gp64 EFP of OpMNPV, and used the cell line to generate a recombinant gp64 efp-null AcMNPV baculovirus. We then examined the effect of the gp64 efp-null mutation on viral transmission in both cell culture and insect larvae.

SUMMARY OF THE INVENTION

The present invention includes a novel baculovirus cloning system. The new cloning system is a marker-rescue system, using an essential gene. In this system, a gene essential for viral replication, growth, or propagation in cell culture is removed from the viral genome. Once a null baculovirus is created it is propagated in a host cell that expresses the essential protein. For cloning into the baculovirus containing the null-mutation, the virus is used to infect wild type host cells and the same cells are transfected with a plasmid that contains the essential gene, or a functional homolog, linked to a foreign gene under the control of a selected promoter. The baculovirus is "rescued" by the rescue gene linked to the foreign gene and is able to propagate normally and express the foreign gene. The recombinant "rescued" baculovirus can be used for gene expression, biological control or presentation of a foreign protein on the surface of the virus for vaccines and antibody production.

The present invention can be practiced with recombinant baculoviruses that contain an insertionally inactivated or deleted gp64 efp gene, a gene that encodes a protein essential for viral infectivity and propagation in cell culture and in animals. To generate the virus the GP64 EFP protein can be supplied in trans, from a stably transfected cell line. Homologous recombination can be used to generate inactivated gp64 efp genes in the context of an otherwise wild type AcMNPV baculoviruses. For generating the stably transfected cell line, a heterologous gp64 efp gene (derived from a different baculovirus, OpMNPV) can be selected. Viruses containing either a) an insertional inactivation of the gp64 efp ORF, or b) a complete deletion of the gp64 ORF were generated by this method.

The function of this gene can be rescued by a tranfection vector including a "rescue" gp64 gene. Such a transfection vector can be a plasmid containing the native AcMNPV gp64 gene. The plasmid can be transfected into wild type Sf9 cells that are infected with a gp64-null baculovirus. The gp64-null virus is rescued when the gp64 efp gene is re-inserted into the viral genome by recombination and a viable baculovirus is obtained after standard virus isolation. The rescue gene can be linked to a foreign gene under the control of an appropriate promoter such that the foreign gene and promoter are also transferred into the baculovirus genome.

This system can be used to create a gp64-null baculovirus for biocontrol or use as a biopesticide with infectivity limited to the insect gut. This "suicide virus" could be propagated in a cell line that expressed a functional equivalent of the GP64 protein, such the infectious null virus could be used as the biological control or biopesticide agent. The infectious null virus would not propagate in the environment, but would cause an infection in the midgut to a single insect that ingested the null baculovirus. This would limit the spread of the engineered null-baculovirus in the environment. This may be desirable if the engineered virus include a gene for a particular toxin of concern or merely to ease concerns about releasing engineered baculoviruses.

Boublik et al., teach that a fusion protein can be made with GP64 and a foreign protein (GP120) and still reach the virus surface for presentation. However, in their system the fusion protein co-expressed with normal GP64. This limits the usefulness of the system for presentation of foreign proteins to an immune system because an immune response would be eventually be generated for the GP64 and use of the system for presenting different proteins to the same animal would be of limited effect. The current system would allow the fusion protein to be expressed on all of the GP64 on the surface. Furthermore, the system could be optimized to limit the amount of GP64 expressed on the surface to the minimum amount necessary to get the fusion protein to the virus surface.

These and other advantages of the present invention will become apparent from the following drawing and detailed description.

DETAILED DESCRIPTION

The present invention involves a series of discoveries made during a study of the role of the baculovirus GP64 Envelope Fusion Protein (GP64 EFP) in the context of a viral infection. To demonstrate the essential nature of the baculovirus GP64 EFP, and to further examine the role of this protein in infection, we inactivated the gp64 efp gene of Autographa californica multicapsid nuclear polyhedrosis virus (AcMNPV), and examined the biological properties of this virus in vivo. To provide gp64 EFP during construction of the recombinant gp64 EFP-null AcMNPV baculovirus, we first generated a stably transfected insect cell line (Sf9$^{OP64-6}$) that constitutively expressed the gp64 EFP of Orgyia pseudotsugata MNPV (OpMNPV).

The AcMNPV gp64 efp gene was inactivated by inserting the bacterial lacZ gene in frame after codon 131 of the gp64 efp gene. The inactivated gp64 gene was cloned into the AcMNPV viral genome by replacement of the wild type gp64 efp locus. When propagated in the stably transfected insect cells (Sf9$^{OP64-6}$), budded virions produced by the recombinant AcMNPV gp64 EFP-null virus (vAc$^{64Z}$) contained OpMNPV gp64 EFP supplied by the Sf9$^{OP64-6}$ cells. Virions propagated in Sf9$^{OP64-6}$ cells were capable of infecting wild type Sf9 cells, and cells infected by vAc$^{64Z}$ exhibited a blue phenotype in the presence of X-gal. Using cytochemical staining to detect vAc$^{64Z}$ infected cells, we demonstrated that this gp64 EFP-null virus is defective for cell to cell propagation in cell culture.

Although defective for cell to cell propagation, vAc$^{64Z}$ produces occlusion bodies and infectious occlusion derived virions within the nucleus. Occlusion bodies collected from cells infected by vAc$^{64Z}$ were infectious to midgut epithelial cells of *Trichoplusia ni* larvae. However, in contrast to a control virus, infection by vAc$^{64Z}$ did not proceed into the hemocoel. Analysis of vAc$^{64Z}$ occlusion bodies in a standard neonate droplet feeding assay showed no viral-induced mortality, indicating that occluded virions produced from vAc$^{64Z}$ could not initiate a productive (lethal) infection in neonate larvae. Thus, GP64 EFP is an essential virion structural protein that is required for propagation of the budded virus from cell to cell and for systemic infection of the host insect.

The deletion of this essential gene led to the discovery of a novel baculovirus cloning system. The new cloning system is a marker-rescue system for an essential gene. An essential gene (gp64 is described herein as an example) is removed from, or inactivated in, the baculovirus genome and the resulting null baculovirus is propagated in a host cell that is stably transfected (or otherwise modified) to express either the native baculovirus gene or a related gene capable of complementing the null mutation in the virus. Virions produced in this manner thus contain a deleted or inactivated essential gene, but contain the essential protein supplied by the cells. These infectious virus particles are used to infect and thus efficiently deliver the null baculovirus DNA to insect cells. To use the essential gene as a selectable marker for cloning into the baculovirus genome, host cells (that do not express the essential protein) are infected with the null baculovirus particles and transfected with a plasmid that contains a functional "rescue" gene (i.e. the gene deleted or inactivated in the null baculovirus) linked to the foreign gene (both under the control of selected promoters). Viral genomic DNA's that acquire the "rescue" gene and the linked foreign gene are thus "rescued" and are able to produce infectious progeny virus particles, whereas genomic DNA's that do not acquire the "rescue" gene are defective and cannot propagate. The baculovirus is "rescued" by the rescue gene linked to the foreign gene and is able to propagate normally and express the foreign gene. The recombinant "rescued" baculovirus can be used for gene expression, biological control or presentation of a foreign protein on the surface of the virus for vaccines and antibody production.

This is a new method for creating a recombinant baculovirus that can express a foreign gene. This system has many advantages over traditional cloning systems: 1) there is a high efficiency of cloning into AcMNPV, 2) there is a high efficiency of delivery of viral genomic DNA to the insect cells, 3) no viral DNA isolation or digestion is required, 4) a true selectable marker for cloning is provided, and 5) the gp64 gene can be combined with a foreign gene such that a foreign protein is presented on the surface of the baculovirus in the absence of a native gp64 gene. The cloning system of the present invention is easier to use than more traditional cloning systems. While this system can be used with other essential genes, so long as there is a means for generating sufficient amounts of the null virus for the cloning system, the gp64 gene is an excellent choice because the gene is essential for production of infectious virions.

Strategy for Initial Generation of Recombinant gp64-null Baculovirus

We generated a recombinant baculovirus that contains an insertionally inactivated gp64 efp gene and examined the effects of that mutation on viral infectivity, and propagation of the virus in cell culture and in animals. Previous studies of the GP64 EFP protein demonstrated that some anti-GP64 antibodies are capable of neutralizing infectivity of the virus. Because of the likelihood that inactivation of the gp64 efp gene would be difficult, we chose to supply the GP64 EFP protein in trans, from a stably transfected cell line, and to then use homologous recombination for generating an inactivated gp64 efp gene in the context of an otherwise wild type AcMNPV baculovirus.

Because a very strong selection pressure for regenerating a gp64 EFP+ virus may result in recombination between the virus and the gp64 efp gene within the cell line, we used the following strategies:

a) For generating the stably transfected cell line, we selected a heterologous gp64 efp gene (derived from a different baculovirus, OpMNPV).
b) Recombinant vAc$^{64Z}$ virus stocks were screened by restriction analysis, Western blots and PCR for significant levels of any revertant virus.
c) A lacZ marker gene was fused in-frame with the wt AcMNPV gp64 efp gene, and analyses of the "loss-of-function" phenotype of the recombinant virus relied on detection of the β-galactosidase marker.
d) We generated a second vAc$^{64Z}$ virus with the gp64 efp ORF completely deleted. The analysis of only cells expressing the lacZ marker gene insured that we exclusively analyzed viruses carrying the inactivated gp64 efp gene.

Generation of Transfected Cell Lines

The first step in the above strategy involved the production of cell lines that constitutively expressed the GP64 EFP protein from OpMNPV. Because previous studies using anti-GP64 EFP antibodies suggested that GP64 EFP might be an essential component of budded virions, we used a strategy in which the GP64 EFP protein was provided in trans, to complement the inactivation of the gp64 efp gene in the virus. To provide GP64 EFP in trans, a stably transfected cell line that constitutively expresses the OpMNPV GP64 EFP protein was generated by transfection with plasmids encoding gp64 EFP and the bacterial neomycin resistance gene, followed by selection for G418 resistance.

Figure 2:
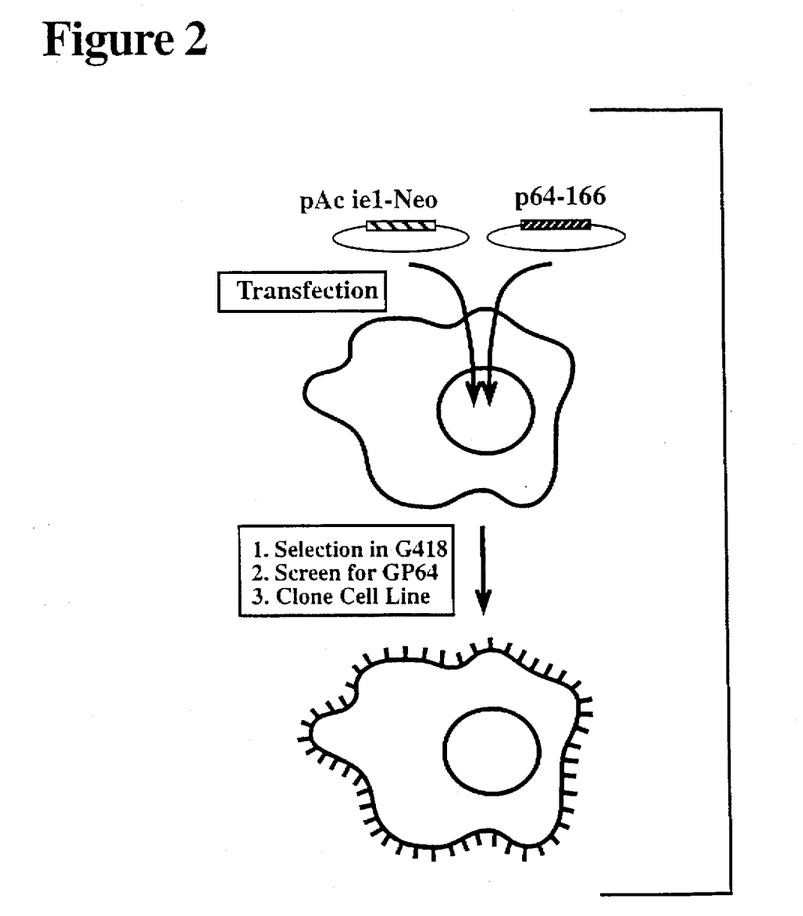
FIG. 2 shows how Sf9 cells were stably transfected with a gp64 gene.
Figure 3:
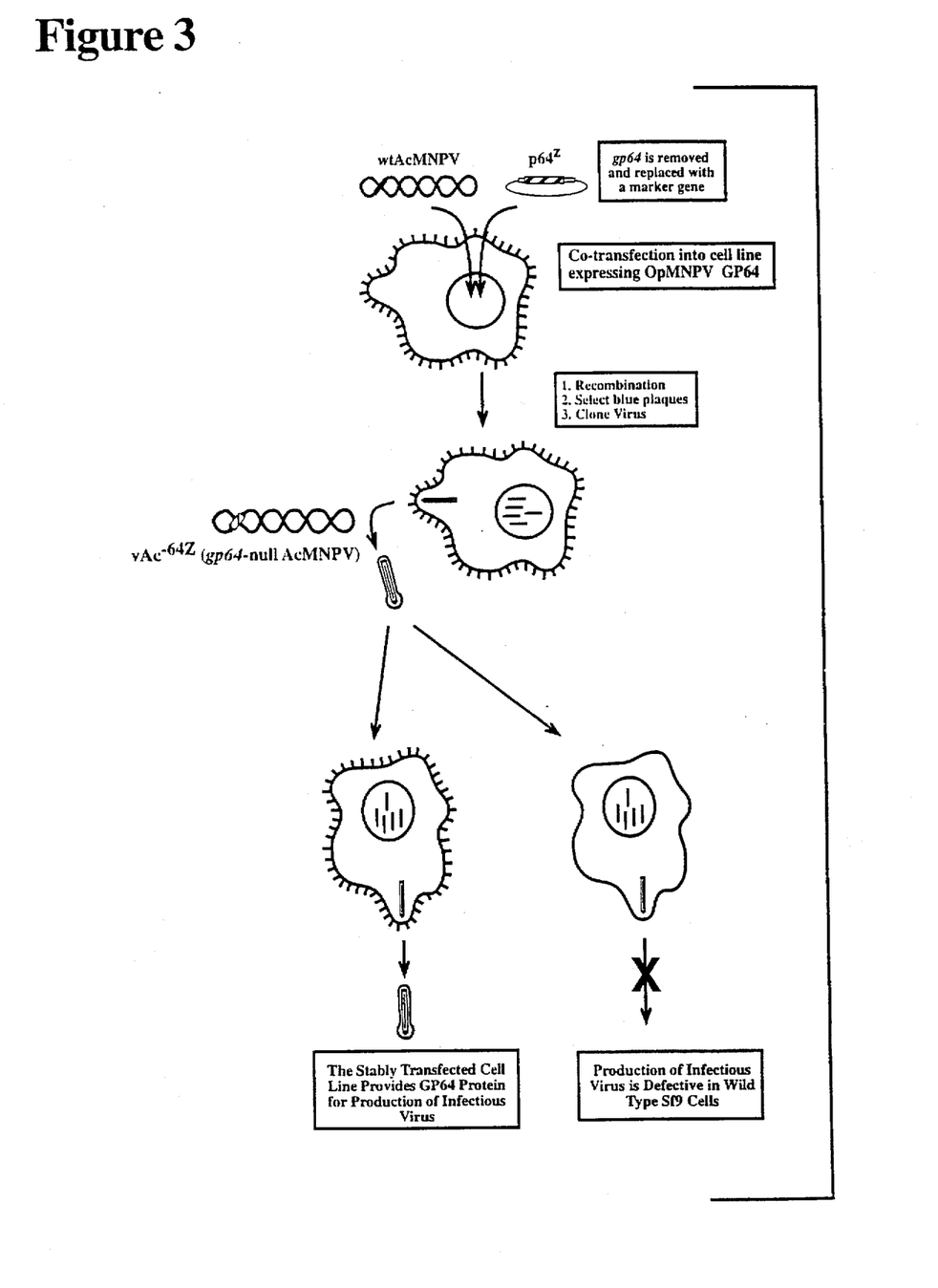
FIG. 3 shows how the gp64-null AcMNPV recombinant baculovirus was created.
Figure 4:
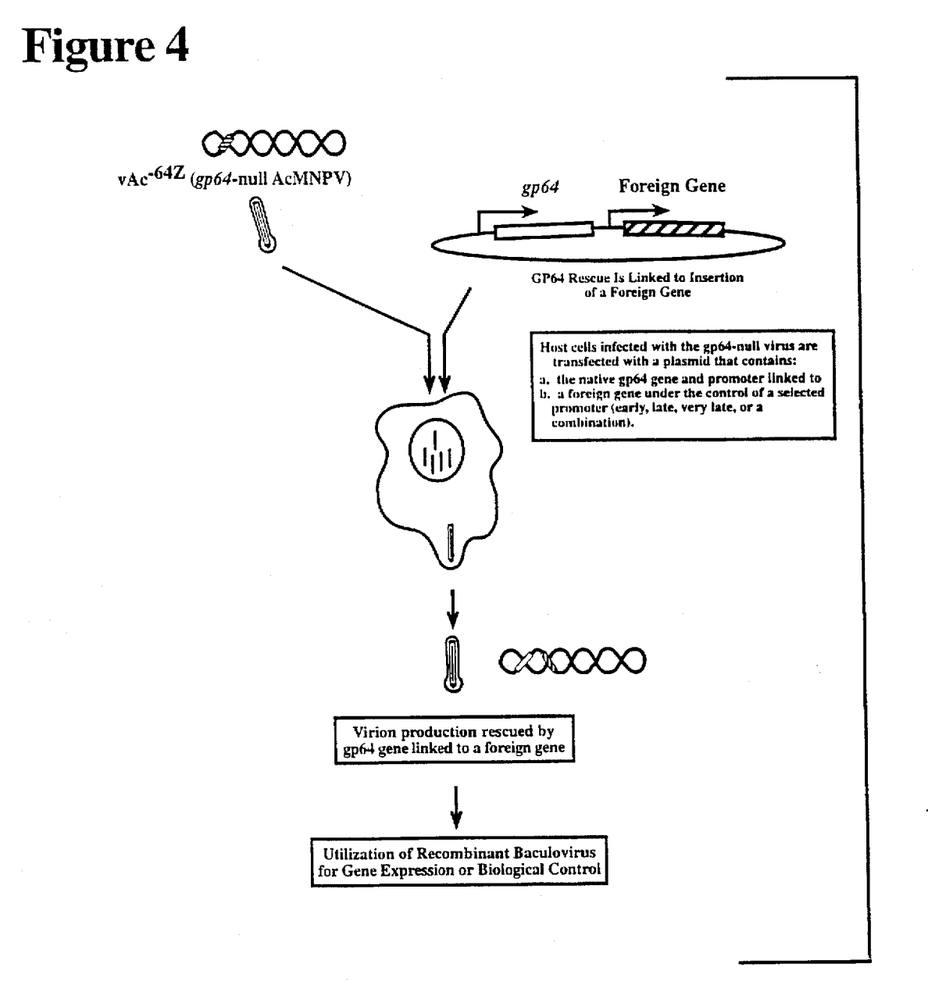
FIG. 4 shows how the gp64-null AcMNPV recombinant baculovirus is used in a marker rescue cloning system of the present invention.

For production of the stably transfected cell lines (and for propagation of AcMNPV), Spodoptera frugiperda Sf9 cells were cultured in TNM-FH complete medium containing 10% fetal bovine serum at 27° C. To express the OpMNPV gp64 EFP, we used a gp64 EFP expression plasmid (p64-166) that contains the OpMNPV gp64 efp ORF under the control of an OpMNPV gp64 efp early promoter construct that has been studied in detail. (See FIG. 2.)

The second plasmid (pAc ie1-Neo) encodes a bacterial neomycin resistance gene under the control of the AcMNPV ie1 promoter, and was constructed using the approach described by Jarvis et al. (1990) Transfected Sf9 cells that were resistant to G418 were selected, and isolated cell lines were established. Transfection and G418 selection were performed essentially as described previously by Jarvis et al. (1995). Briefly, Sf9 cells were plated at a density of 1×10$^6$ cells per well (34 mm diameter). The cells were transfected with 2 μg p64-166 plasmid plus 1 μg pAc ie1-Neo using calcium phosphate precipitation. One day after transfection, the cells were replated at low density in 75 cm$^2$ flasks and maintained for 2 weeks in TNM-FH complete media containing 1 mg/ml G418 (Geneticin, GIBCO-BRL). During this period, mock-transfected Sf9 control cells died due to the G418 selection. The G418-resistant transfected cells were replated in TNM-FH complete medium (lacking G418) at low density. Single colonies were isolated and transferred to individual wells of a 24 well plate. Isolated lines were screened for gp64 EFP expression by cell-surface staining of paraformaldehyde-fixed cells using MAb AcV5 and an alkaline phosphatase-conjugated goat-anti-mouse secondary antibody. Isolated lines were also screened for GP64 EFP fusion activity using a syncytium formation assay.

Analysis of GP64 EFP Expression in Transfected Cell Lines

In addition to facilitating the construction of the recombinant virus, the use of a heterologous gp64 efp gene also allowed us to determine whether the highly conserved (but not identical) OpMNPV GP64 EFP could functionally replace the AcMNPV GP64 EFP protein. After constructing the OpMNPV GP64 EFP expressing cell lines, we performed several quantitative studies to compare GP64 EFP expression from AcMNPV infected cells, stably transfected cells and transiently transfected cells.

The expression of GP64 EFP from two stably transfected cell lines (Sf9$^{OP64-6}$ and Sf9$^{OP64-2}$) was compared to AcMNPV infected Sf9 cells (at 24 h pi), and to transient GP64 EFP expression from Sf9 cells transfected with plasmid p64-166 (at 44 h post-transfection). For these analyses, we used several quantitative techniques to determine absolute and relative levels of GP64 EFP: a) absolute levels of GP64 EFP from whole cells were determined by quantitative ECL-Western blots, b) relative surface levels of GP64 EFP were determined by CELISA, and c) variation in average surface density of GP64 EFP was determined by flow cytometry.

We measured the quantities of GP64 EFP expressed on a per cell basis. A soluble secreted form of GP64 EFP (GP64 EFP$^{sol}$) was used to generate a standard curve for quantitative ECL analysis. The quantity of GP64 EFP detected in AcMNPV infected Sf9 cells at 24 h pi corresponds to approximately 1.3×10$^6$ trimers of GP64 EFP per cell. The quantity of GP64 EFP detected from stably transfected line Sf9$^{OP64-6}$ (2.5×10$^5$ trimers/cell) was approximately 19% of that detected from AcMNPV infected cells at 24 h pi. Total GP64 EFP levels from line Sf9$^{OP64-2}$ were lower (1.6×10$^5$ trimers/cell), corresponding to approximately 12% of that detected from AcMNPV infected cells. Interestingly, transiently transfected Sf9 cells assayed at 44 h post-transfection (included as a control) showed the highest average levels of GP64 EFP expression, approximately 3.2×10$^6$ trimers/cell, or 2.5 times that detected from AcMNPV infected Sf9 cells.

While the total quantity of GP64 EFP per infected cell was approximately 5 times higher than the quantity detected per Sf9$^{OP64-6}$ cell, a further (CELISA) analysis of the average levels of GP64 EFP at the surface of these cells indicated that the level of GP64 EFP at the surface of the Sf9$^{OP64-6}$ cells was similar to that of infected cells. Detection and quantification (by CELISA) of average relative levels of surface-localized GP64 EFP showed that the level of surface-localized GP64 EFP from Sf9$^{OP64-6}$ cells was similar to that detected at the surface of AcMNPV infected Sf9 cells at 24 h pi, a time when virion budding is occurring. Average surface levels of GP64 EFP on Sf9$^{OP64-2}$ cells were lower, corresponding to approximately 70% of that detected from AcMNPV infected Sf9 cells or Sf9$^{OP64-6}$ cells. Transiently transfected Sf9 cells assayed at 44 h post-transfection expressed the highest average levels of surface GP64 EFP, corresponding to approximately 2.7 times that detected from AcMNPV infected Sf9 cells at 24 h pi.

Because GP64 EFP expression levels may vary between individual cells in a population, we also used flow cytometry to determine the degree of variation. The degree of variation (of GP64 EFP surface densities) within populations was compared between AcMNPV infected Sf9 cells at 24 h pi, stably transfected cell lines (SF9$^{OP64-6}$ and Sf9$^{OP64-2}$), and transiently transfected cells at 44 h post-transfection. Analysis of cells from each population showed that both stably transfected cell lines (Sf9$^{OP64-6}$ and Sf9$^{64-2}$) and transiently transfected Sf9 cells contain a significantly wider variation in GP64 EFP surface densities than do AcMNPV infected Sf9 cells. A small proportion of cells in both of the stably transfected cell populations and in the transiently transfected cell population showed higher levels of surface GP64 EFP (relative fluorescence intensities of approximately 200–300) than did infected Sf9 cells (maximum fluorescence intensity of approximately 150). The flow cytometry analysis of surface GP64 EFP levels on individual cells in each population indicated that there was less cell to cell variability among AcMNPV infected cells than among SF9$^{OP64-6}$ cells.

Greater variability of GP64 EFP surface density appeared to be a general feature of transfected cells, since both the Sf9$^{OP64-2}$ cell line and transiently transfected cells also exhibited wider variations in GP64 EFP surface levels. The narrower range of GP64 EFP surface levels in infected Sf9 cells is likely due to the synchronization of GP64 EFP expression during infection, since at 24 hours postinfection, GP64 EFP expression is primarily from the late promoter. In contrast, GP64 EFP in transfected cells results from constitutive expression by the early promoter and accumulation of the protein in a population of asynchronously dividing cells. In transient transfections, variable levels of GP64 EFP expression may also arise from cell to cell variations in DNA uptake during transfection.

Because cell surface levels of GP64 EFP from infected and Sf9$^{OP64-6}$ cells were similar, yet an approximately 5 fold difference was detected in the total quantity of GP64 EFP, these data suggest that no more than 20% of the total GP64 EFP protein detected from AcMNPV infected Sf9 cells (at 24 h pi) is found at the cell surface. Using this estimate of surface localization (20%) in combination with quantitative ECL data derived from whole cell measurements of GP64 EFP, we estimate that AcMNPV infected Sf9 cells (MOI 10, 24 h pi) contain an average surface density of $2.6 \times 10^5$ trimers of GP64 EFP per cell, at most.

Thus by several measurements, the average surface density of GP64 EFP on stably transfected Sf9$^{OP64-6}$ cells appears to be comparable to that on AcMNPV infected Sf9 cells at 24 h pi, a time at which active budding of virions is occurring. Therefore, the level of GP64 EFP expressed by Sf9$^{OP64-6}$ cells was judged to be sufficient to complement inactivation of the gp64 efp gene in the AcMNPV viral genome.

Generation of a gp64 EFP-null AcMNPV Baculovirus

Viral DNA used for the generation of recombinant viruses was prepared from the E2 strain of AcMNPV by standard methods. For production of budded virus (BV) stocks and occlusion bodies of the wild type and recombinant viruses, cells (Sf9 or Sf9$^{OP64-6}$) were infected at a multiplicity of infection (MOI) of 0.1 and incubated at 27° C. for 5 to 7 days. Supernatants were harvested and titred by end-point dilution. The recombinant AcMNPV virus lacking GP64 expression was titred on the Sf9$^{OP64-6}$ cells, and the wild type AcMNPV virus and recombinant virus vAc$^{hsZ}$ were titred on Sf9 cells. Occlusion bodies were purified from infected cells by sequential washing with 0.5% SDS, 0.5M NaCl and distilled water. For analysis of budded virion structural proteins, budded virions were isolated from viral stocks by pelleting through a 25% sucrose pad followed by centrifugation on 25%–60% sucrose gradients. The budded virus band was collected, diluted in PBS pH 6.2, pelleted and resuspended in SDS lysis buffer for SDS-PAGE on 10% acrylamide gels.

Figure 1:
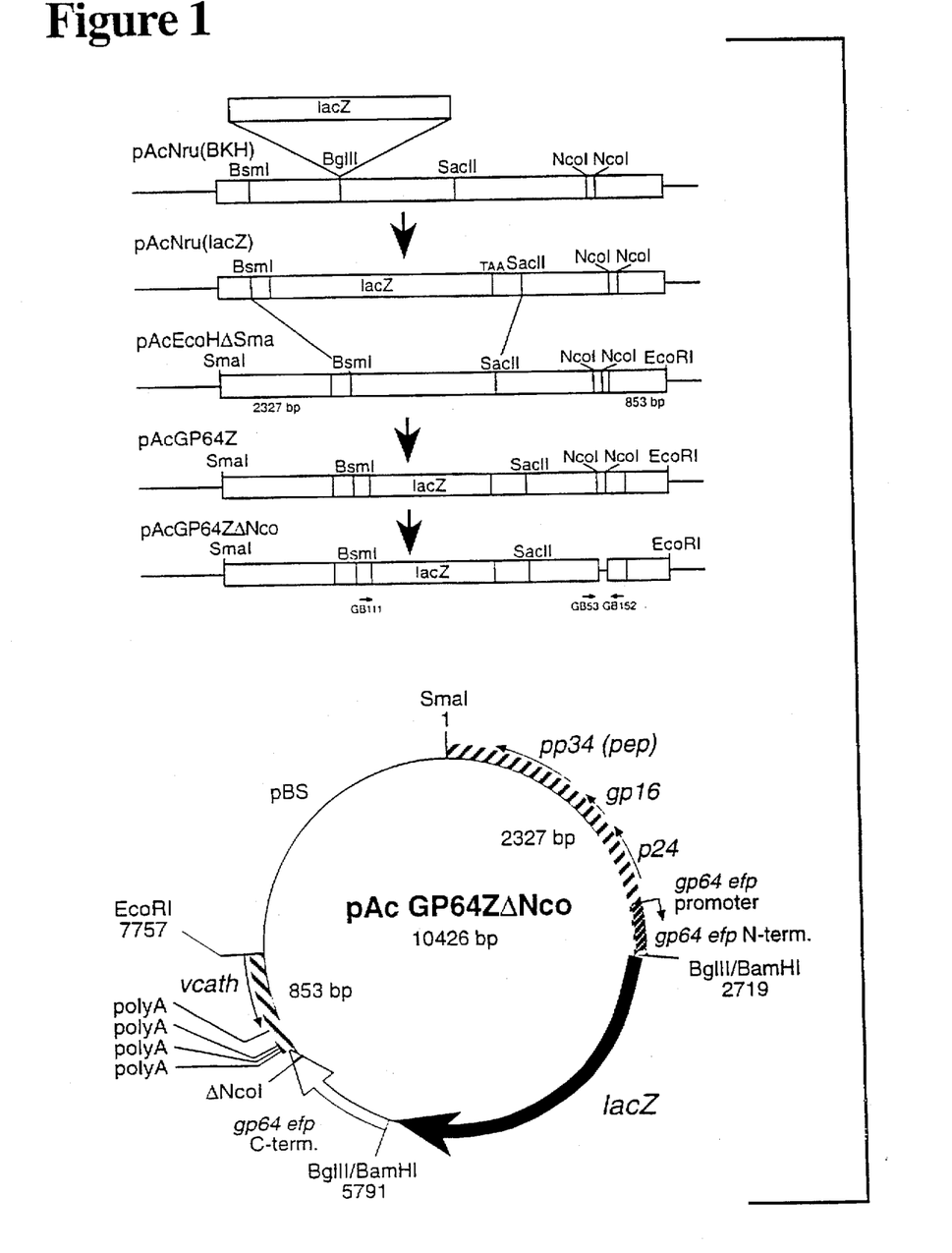
FIG. 1 shows how the AcMNPV gp64 efp gene was inactivated by inserting the bacterial lacZ ORF (in frame) into the gp64 efp ORF after codon 131.

To inactivate the gp64 efp gene in AcMNPV, we used insertional mutagenesis. The AcMNPV gp64 efp gene was inactivated by inserting the bacterial lacZ ORF (in frame) into the gp64 efp ORF after codon 131 as shown in FIG. 1. Although the lacZ ORF contains a translation termination codon, we also created a frame-shift mutation after codon 452 of gp64 efp, by removing a 54 bp NcoI restriction fragment. This frame shift resulted in a translation termination codon immediately upstream of the gp64 EFP transmembrane domain and insured inactivation of the gp64 efp gene. The gp64-lacZ fusion gene was then cloned into a transfer vector containing sequences flanking the gp64 efp locus in AcMNPV. Recombination of this transfer vector into the gp64 efp locus of wild type AcMNPV results in a virus wild type for all genes except gp64 efp.

To construct the transfer vector for allelic replacement of the gp64 efp locus of the AcMNPV genome, the 4718 bp EcoRI-SmaI fragment (corresponding to nucleotides 107, 326 to 112,043 from the EcoRI H fragment) of AcMNPV strain E2 was cloned into the pBS vector (Stratagene) to generate the plasmid pAcEcoHΔSma. This plasmid contains 2327 bp upstream of the gp64 efp ORF, the gp64 efp ORF, and 853 bp downstream of the gp64 efp ORF. To disrupt the AcMNPV gp64 efp gene by insertional mutagenesis, we generated an in-frame fusion between gp64 EFP and the Escherichia coli lacZ gene in an AcMNPV gp64 EFP expression plasmid pAcNru(BKH). The pAcNru(BKH) expression plasmid contains an 18 bp in-frame linker encoding unique BglII, KpnI and HindIII restriction sites, inserted at the NruI restriction site within the gp64 efp ORF of plasmid p166B+1 Ac Spe/Bgl. A 3072 bp BamHI fragment containing the lacZ ORF (derived from pMC1871) was subcloned into BglII digested pAcNru(BKH). The resulting construct (pAcNru(lacZ)) contains a gp64-lacZ fusion after codon 131 of gp64 efp, and the fusion gene open reading frame terminates at the end of the lacZ insertion. The 3447 bp BsmI/SacII fragment of pAcNru(lacZ) (containing the lacZ cassette and the flanking portions of gp64 efp) was subcloned into BsmI/SacII digested pAcEcoHΔSma, to generate plasmid pAcgp64Z. Finally, to ensure inactivation of the gp64 efp gene, the downstream portion of the gp64 efp ORF was truncated by digesting pAcgp64Z with NcoI, removing the resulting 54 bp NcoI-NcoI fragment, then blunting and religating to generate pAcgp64ZΔNco. This deletion results in a frame shift mutation and terminates the gp64 efp open reading frame after codon 452, 30 codons upstream of the predicted transmembrane domain.

FIG. 1 shows the construction of the gp64-lacZ transfer vector pAcgp64ZΔNco. Plasmid names are indicated for each construct (diagrams not to scale). Small arrows below the bottom diagram indicate the locations of primers (SEQ ID:1 (GB 111), SEQ ID:3 (GB 53), SEQ ID:2 (GB 152)) used for PCR analysis. A map of the gp64-lacZ transfer vector pAcgp64ZΔNco is shown. The transfer vector contains 2327 bp of flanking sequences upstream of the gp64 efp ORF, and 853 bp of flanking sequences downstream of the wild type gp64 efp stop codon. Also indicated are the locations and orientations of genes flanking the gp64 efp locus (vcath, p24, gp16 and pp34 (pep)).

Recombinant viruses were generated using standard protocols, by co-transfecting viral DNA from wild-type AcMNPV strain E2 and pAcgp64ZΔNco plasmid DNA into the gp64 EFP expressing SF9$^{OP64-6}$ cells. A recombinant virus (vAc$^{64Z}$) was isolated from culture supernatant by plaque purification on SF9$^{OP64-6}$ cells, using X-gal in the agarose overlay to identify the recombinant plaques.

The structure of the gp64 efp locus in vAc$^{64Z}$ was analyzed by PCR amplification and restriction mapping. DNA was extracted from infected Sf9 cells at 24 h pi, or viral DNA was isolated from BV pelleted through a 25% sucrose cushion. For PCR analysis, the following primers homologous to the 5' and 3' ends of the gp64 efp ORF were used:

SEQ ID:1 (GB 111), 5'-GAGCTGATCGACCGTTGGGG-3'; and
SEQ ID:2 (GB 152), 5'-CGGTTTCTGATCATACAGTACA-3'.

To verify the presence of the NcoI deletion in vAc$^{64Z}$, PCR amplification was performed using primers flanking the deletion site:

SEQ ID:3 (GB 53), 5'-CCAGCGGCTGGTCGTTTATCGCCC-3'; and
SEQ ID:2 (GB 152).

For comparisons of infection in Sf9 cells and *T. ni* larvae, a control virus (vAchsZ; kindly provided by Dr. P. Roelvink) was used. vAc$^{hsZ}$ contains the bacterial lacZ gene (under the control of the Drosophila hsp70 promoter) in the p10 locus, and lacks a functional p10 gene (vAc$^{hsZ}$ is identical to recombinant virus AcNPV/As3).

To generate recombinant viruses defective for gp64 EFP, transfections, recombination and viral growth were carried out in the Sf9$^{OP64-6}$ cell line. A recombinant virus (vAc$^{64Z}$) was isolated by plaque purification on SF9$^{OP64-6}$ cells, using X-gal in the plaque overlay to detect β-galactosidase expression. Although the gp64 efp promoter is active in both early and late phases of infection, β-galactosidase activity was not detectable before 5-7 days pi, unless the plaque assay plates were subjected to a freeze-thaw cycle to disrupt the infected cells. This result suggested that active gp64-β-galactosidase fusion protein was not secreted into the medium, despite the presence of the gp64 EFP signal peptide in the GP64-β-galactosidase fusion protein.

To confirm the location of the gp64-lacZ insertion in vAc$^{64Z}$, the gp64 efp locus of the vAc$^{64Z}$ recombinant virus was examined by PCR amplification using primers complementary to the 5' and 3' ends of the gp64 efp gene. As control templates for PCR, we used a plasmid containing the wild-type AcMNPV gp64 efp gene (negative control), DNA from cells infected with wild type AcMNPV, or plasmid DNA of the transfer vector pAcgp64ZΔNco (positive control). Amplification from the plasmid containing the wild type gp64 efp gene or AcMNPV viral DNA resulted in a 1.17 kb product, as predicted from the sequence. Amplification from the pAcgp64ZΔNco transfer vector or DNA from cells infected by vAc$^{64Z}$ resulted in a single 4.22 kb product, as predicted from allelic replacement of the gp64 efp locus by the gp64-lacZ fusion gene. PCR analysis (using primers SEQ ID:3 (GB 53) and SEQ ID:2 (GB 152)) was also used to verify that the recombinant virus vAc$^{64Z}$ lacked the NcoI fragment deleted from the downstream region of the gp64 efp ORF. The structure of the recombinant virus vAc$^{64Z}$ was also examined by restriction enzyme digestion of viral genomic DNA. As expected, the EcoRI and BamHI restriction profile of vAc$^{64Z}$ differed from wild type AcMNPV only in the EcoRI H and BamHI G fragments, confirming replacement of the gp64 efp locus. Thus, PCR analysis, restriction mapping and β-galactosidase activity indicate that the recombinant virus vAc$^{64Z}$ contains only the gp64-lacZ fusion gene in the gp64 efp locus, and cells infected with vAc$^{64Z}$ express β-galactosidase activity.

To verify that the gp64 efp gene was inactivated, vAc$^{64Z}$ infected Sf9 cells were examined by ECL-Western blot analysis. Cells were infected with either vAC$^{64Z}$ or wild type AcMNPV, and cell lysates were prepared at 24 and 48 h pi. Replicate blots were probed with monoclonal antibodies specific to β-galactosidase, GP64 EFP, or P39 capsid protein. A replicate blot was also probed with a mixture of all three antibodies. Expression of β-galactosidase was detected only in cells infected with vAc$^{64Z}$ and not in cells infected with wild type AcMNPV. GP64 EFP expression was not detectable in cells infected with vAc$^{64Z}$. However, expression of the capsid protein P39 was detected in cells infected with either vAc$^{64Z}$ or wild type AcMNPV.

To demonstrate the presence of OpMNPV GP64 EFP on budded virions produced by vAc$^{64Z}$ infected Sf9$^{OP64-6}$ cells, budded virions were purified from tissue culture supernatants by sucrose gradient centrifugation and examined by Western blot analysis. As a control, budded virions were also purified from tissue culture supernatants of AcMNPV infected Sf9 cells. Replicate blots were probed with either a) a monoclonal antibody that reacts only with the OpMNPV GP64 EFP, b) a monoclonal antibody that reacts with GP64 EFPs of both OpMNPV and AcMNPV, or c) a monoclonal antibody that reacts with the P39 capsid protein. GP64 EFP was detected in purified budded virions of both AcMNPV and vAc$^{64Z}$ by monoclonal antibody AcV5 (which cross reacts with GP64 EFPs of both AcMNPV and OpMNPV), and capsid protein P39 was also detected in both budded virion preparations. Using the OpMNPV GP64 EFP-specific monoclonal antibody (OpE4A), we detected the OpMNPV GP64 EFP in purified budded virions of vAc$^{64Z}$, but not in budded virions of AcMNPV. Thus vAc$^{64Z}$ budded virions produced from SF9$^{OP64-6}$ cells contained the OpMNPV GP64 EFP protein.

To verify that the infection cycle proceeds normally in vAc$^{64Z}$ infected cells, the kinetics of the infection cycle were examined by pulse-labeling of proteins. In vAc$^{64Z}$ infected Sf9 cells, the overall pattern of protein synthesis was similar to that from Sf9 cells infected with wt AcMNPV. At 24 h pi, a labeled band of approximately 64 kD was observed in wt AcMNPV infected cells but not in vAc$^{64Z}$ infected cells. Because 24 h pi is the time of maximal GP64 EFP synthesis in AcMNPV infected Sf9 cells, this 64 kD band is likely GP64 EFP. Comparison of the temporal progression of infection confirms progression into the late phase between 6 and 12 h pi and therefore suggests that the viral infection cycle of vAc$^{64Z}$ is not significantly affected by the lack of GP64 EFP expression.

Because sequences flanking the gp64 efp genes of AcMNPV and OpMNPV are present in the recombinant virus vAc$^{64Z}$ and in the Sf9$^{OP64-6}$ cell line, respectively, and the two genes are highly similar, the formal possibility exists that recombination between the heterologous genes in the virus and cell line might result in replacement of the gp64-lacZ fusion gene with a functional (OpMNPV) gp64 EFP gene. In addition, selection pressure might force integration of the OpMNPV gp64 EFP gene at random sites within the genome. Such recombination products were not detected in DNA from the vAc$^{64Z}$ viral stocks, using PCR amplification with primers specific for the OpMNPV gp64 efp gene. In control experiments, OpMNPV viral DNA was detectable with the OpMNPV specific primers when mixed with AcMNPV DNA at a molar ratio of 1 part OpMNPV to $10^4$ parts AcMNPV DNA, but was not detectable at $1:10^5$.

Our inability to detect OpMNPV gp64 efp in vAc$^{64Z}$ viral stocks therefore indicates that if any recombinant viruses carrying the OpMNPV gp64 efp gene were present, they occurred at a frequency of less than 1 in $10^4$ particles. Because the most likely recombination events that might restore the gp64 efp gene would also remove the lacZ gene, expression of the lacZ marker gene was used as the indicator of infection in subsequent analyses of vAc$^{64Z}$ infectivity.

Production of infectious vAc$^{64Z}$ budded virus from Sf9$^{OP64-6}$ cells was on the order of 2–3×10$^7$ infectious units/ml (determined by TCID50 on Sf9$^{OP64-6}$ cells). The presence of gp64 EFP on the surface of the Sf9$^{OP64-6}$ cells apparently did not interfere with infection, since the TCID50 titer of the wild type AcMNPV stock determined on the Sf9$^{OP64-6}$ cells was approximately 1.3 fold higher than the titer determined on Sf9 cells. In addition to production of recombinant baculoviruses containing deletions or mutations in gp64 EFP, these stably transfected cell lines constitutively expressing gp64 EFP will also be useful for studies of gp64 EFP mediated membrane fusion. gp64 efp is an essential baculovirus gene.

The production of infectious budded virions by vAc$^{64Z}$ infected Sf9$^{OP64-6}$ cells demonstrates that the OpMNPV gp64 EFP can functionally substitute for the AcMNPV gp64 EFP in the production of budded virions. In addition, vAc$^{64Z}$ virions (produced in SF$^{OP64-6}$ cells) were infectious to Sf9 cells indicating that this aspect of host range was apparently unaffected. Thus the GP64 EFP protein from these two related baculoviruses appears to be interchangeable. Of particular importance, we demonstrate that vAc$^{64Z}$ budded virions produced in Sf9$^{OP64-6}$ cells are able to enter and infect Sf9 cells, but in the absence of the gp64 efp gene, the vAc$^{64Z}$ virus is unable to transmit the infection to uninfected neighboring cells. Thus gp64 efp is an essential baculovirus gene, and the GP64 EFP protein is required for the cell to cell transmission of the infection. Studies are now in progress to identify the cause of the defect in viral transmission. Preliminary studies suggest that virion budding is defective in the absence of GP64 EFP.

In previous studies, the transmission of virus from the midgut to hemocoel has been studied using marker genes to follow the progression of tissues infected. Virions have been observed budding from the basal side of the midgut epithelial cells and virion budding is believed to serve as the primary mode of viral movement from midgut epithelium to hemocoel. Hemocytes, cells of the tracheal system, and basal lamina associated muscle and tracheal cells have been proposed as the primary cells infected after the first round of replication in midgut epithelial cells. It has also recently been suggested that the tracheal system may serve as a route for budded virus transmission across the basal lamina of the midgut epithelium to other tissues within the hemocoel.

We examined the role of GP64 EFP during infection in the animal by feeding occlusion bodies prepared from vAc$^{64Z}$ infected cells to either neonate or early 4th instar T. ni larvae. Using whole mount histological staining of 4th instar T. ni larvae to detect infection, we found that the vAc$^{64Z}$ occlusion derived virions were capable of infecting cells of the midgut epithelium, but infection by vAc$^{64Z}$ did not move beyond the midgut. The ability of vAc$^{64Z}$ to produce infectious occluded virions in the absence of GP64 EFP expression is consistent with previous studies that found no detectable GP64 EFP protein associated with the occluded virus, and clearly demonstrates the virion phenotype specificity of the GP64 EFP protein.

As perhaps the most sensitive indicator of systemic propagation of viral infection, we examined mortality in neonate larvae fed occlusion bodies of vAc$^{64Z}$. At doses of up to 100× the LD65 of AcMNPV, the vAC$^{64Z}$ virus was non-lethal to T. ni neonates. The lack of vAc$^{64Z}$ induced mortality in T. ni neonate larvae thus confirms the observations in tissues of whole 4th instar larvae, and demonstrates that the inability of the vAc$^{64Z}$ virus to escape from the midgut epithelium results in a non-lethal phenotype in the animal. These results therefore demonstrate an absolute requirement for GP64 EFP in the progression of the infection from the midgut epithelium to the systemic form of the disease in tissues of the hemocoel.

The deletion of this essential gene led to the development and discovery of a novel baculovirus cloning system and a novel strategy for biopesticide delivery. As stated above, the new cloning system is a marker-rescue system for an essential gene, and in this example GP64 EFP was selected. Once the gp64-null baculovirus is created, (e.g. gp64-null AcMNPV) it can be propagated in a transfected cell line expressing a gp64 gene from the same or a different baculovirus (e.g. OpMNPV). This provides an infectious virus that can be used to infect a cell line, but will not lead to production of new virus particles in a wild type cell line unless gp64 expression is "rescued". To rescue gp64, gp64-null virus infected wild type cells are transfected with a plasmid that contains a gp64 gene construct and the virus is rescued by recombination. For cloning foreign genes, the rescue of gp64 expression is linked to a foreign gene. This can be accomplished by linking a foreign gene (under control of an appropriate promoter) to the gp64 gene construct on the same plasmid and providing sequences for recombination such that recombination occurs at sites flanking the two genes or otherwise results in insertion of both genes into the viral genome. The baculovirus is "rescued" by the rescue gene linked to the foreign gene, thus resulting in a baculovirus that has acquired the foreign gene and now is able to propagate normally and express the foreign gene. The recombinant "rescued" baculovirus can be used for gene expression, biological control as a biopesticide or for the presentation of a foreign protein on the surface of the virus for vaccines and antibody production.

This is a new method for creating a recombinant baculovirus that can express a foreign gene. This system eliminates the isolation and use of viral genomic DNA for baculovirus cloning. Problems and difficulties associated with the use of viral genomic DNA include: linearization with restriction enzymes, quality control testing of digestion and DNA quality (for integrity and transfection), and concerns with storage, nucleases, etc. A decrease of 50–80% in the commercial cost of producing the necessary reagents for a baculovirus cloning system can be realized by implementation of this marker-rescue cloning system. Furthermore, commercial suppliers of cloning systems can provide kits with the cell lines, plasmids and baculovirus necessary for the cloning system in one package. While this was possible before, the present system will need the recombinant cell line expressing the heterologous protein for production of infectious null baculovirus to be "rescued". Therefore, the consumer will need to continue to purchase the infectious null baculovirus from the company, because without the infectious null baculovirus cannot be produced recombinant cell line.

Once optimized, the efficiency of cloning into baculovirus genomes will be improved with the cloning system of the present invention. The efficiency of virion entry into host cells is far more efficient than transfection of the isolated circular or linear DNA genome of baculovirus which range from approximately 90–180 kbp. The virus is evolutionarily designed to efficiently deliver DNA to the nucleus of its host cell, whereas artificial transfection of such large DNA (especially linearized DNA) is extremely inefficient.

Because engineering some baculovirus genomes is problematic due to the large size of the genoine (up to 180 kbp), this system eliminates the problems of poor transfection efficiencies and the need to repeatedly isolate and linearize genomic DNA.

This system can be used with other essential genes, so long as there is a means for generating sufficient amounts of the null virus for the cloning system. The gp64 gene is an excellent choice because the gene is essential for production of infectious virions. Other genes that may prove similarly useful for generating viruses with null-mutations and similar rescue strategies include other genes that are essential or important for viral structure, replication or propagation in cell culture. Such genes may include capsid protein genes (vp 39, p80/87, p24 or p78/83), other as yet uncharacterized envelope protein genes form the budded form of the virus or essential regulatory genes such as ie-1, ie-N, (ie-2), and lef genes. Other mutations that render the expression of these genes may be possible. For example deletion or inactivation of promoters or other control elements for essential genes could accomplish the same purpose.

This system can be used to develop cloning systems for an number of baculoviruses. The gp64 gene has been isolated and sequenced in a number of baculoviruses. For example, cloning systems could be created from the teachings herein and information available in the literature for the following systems: *Orgyia pseudotsugata* MNPV (OpMNPV), *Trichoplusia ni* SNPV (TnSNPV), *Lymantria dispar* MNPV (LdMNPV), *Choristoneura fumiferana* MNPV (CfMNPV), *Bombyx mori* NPV (BmNPV), and other baculoviruses.

Accordingly, it is to be understood that the embodiments of the invention herein described are merely illustrative of the application of the principles of the invention. Reference herein to details of the illustrated embodiments are not intended to limit the scope of the claims, which themselves recite those features regarded as essential to the invention.

What is claimed is:

1. A method of cloning DNA into a nuclear polyhedrosis virus comprising the following steps:
   a) obtaining and propagating in modified and stably transfected host cells, infectious nuclear polyhedrosis virus particles that include a null mutation such that the genome of said infectious nuclear polyhedrosis virus particles lack a functional essential gene for production or propagation of infectious virus particles in wild type host cells, but can be propagated in said modified and stably transfected host cells expressing a gene that allows production of infectious null-nuclear polyhedrosis virus particles;
   b) obtaining a rescue transfection vector that includes within its genetic material said DNA to be cloned and a rescue DNA that restores function of said functional essential gene lacking in said null-nuclear polyhedrosis virus;
   c) infecting host cells with said infectious null-nuclear polyhedrosis virus particles and transfecting with said rescue transfection vector;
   d) culturing said transfected and infected host cells to select for recombinant nuclear polyhedrosis virus particles that express said rescue DNA; and
   e) harvesting said recombinant nuclear polyhedrosis virus particles that express said rescue DNA.

2. The method of claim 1 wherein said rescue DNA is linked to a foreign gene under the control of an appropriate promoter such that said foreign gene is expressed when said harvested recombinant baculovirus particles are used to infect host cells.

3. The method of claim 1 wherein said essential gene is gp64 and said modified host cell expresses a gp64 gene.

4. An improved method of cloning DNA into a nuclear polyhedrosis virus by providing said DNA to be cloned in said nuclear polyhedrosis virus within a host cell and providing viral genomic DNA for said nuclear polyhedrosis virus with said host cell, wherein said improvement comprises:
   a) providing said viral genomic DNA to said host cell with an infectious null-nuclear polyhedrosis virus particle that includes a viral genome mutation such that said infectious null-nuclear polyhedrosis virus particle lacks a functional essential gene for production of an infectious virus particle in wild type host cells, but can be propagated in modified host cells expressing a gene that allows production of infectious virus particles; and
   b) said DNA to be cloned into said nuclear polyhedrosis virus includes a rescue DNA that restores function of said functional essential gene lacking in said null-nuclear polyhedrosis virus.

5. The method of claim 4 wherein said rescue DNA is linked to a foreign gene under the control of an appropriate promoter such that said foreign gene is expressed when said harvested recombinant baculovirus particles are used to infect host cells.

6. The method of claim 4 wherein said essential gene is gp64 and said modified host cell expresses a gp64 gene.

7. An infectious null-nuclear polyhedrosis virus particle that includes a mutation such that said infectious nuclear polyhedrosis virus particle lacks a functional essential gene for production of an infectious virus particle in wild type host cells, but can be propagated in modified host cells expressing a gene that allows production of infectious virus particles.

8. The null-nuclear polyhedrosis virus of claim 7 wherein said essential gene is gp64 and said modified host cell expresses a gp64 gene.

9. A modified host cell that expresses a gene that allows production of infectious nuclear polyhedrosis virus particles when infected with an infectious null-nuclear polyhedrosis virus particle that includes a mutation such that said infectious nuclear polyhedrosis baculovirus particle lacks a functional essential gene for production of infectious virus particles in wild type host cells.

10. The cell of claim 9 wherein said functional essential gene lacking in said nuclear polyhedrosis virus particle is a gp64 gene and said modified host cell expresses a gp64 gene.

11. A transfer vector that includes a rescue DNA that restores permanent function of an essential gene that has been inactivated or deleted in a nuclear polyhedrosis baculovirus such that said nuclear polyhedrosis baculovirus can not produce infectious virus particles in wild type host cells, but can be propagated in modified host cells expressing a gene that allows production of infectious virus particles, when said nuclear polyhedrosis baculovirus and said transfer vector are used to co-transfect a host cell and produce recombinant baculovirus particles.

12. The transfer vector of claim 11 wherein said rescue DNA is linked to a foreign gene under the control of an appropriate promoter such that said foreign gene is expressed when said recombinant baculovirus particles are used to infect host cells.

13. The transfer vector of claim 12 wherein said rescue DNA is DNA that restores function of a gp64 gene.

* * * * *